United States Patent
Roberts et al.

(10) Patent No.: US 6,306,831 B1
(45) Date of Patent: Oct. 23, 2001

(54) TRANSPLACENTAL DELIVERY OF OLIGONUCLEOTIDES

(75) Inventors: Peter C. Roberts, Holliston; Samuel E. Driver, Brighton, both of MA (US)

(73) Assignee: QIK Technologies, Inc., Providence, RI (US)

( * ) Notice: Subject to any disclaimer, the term of this patent is extended or adjusted under 35 U.S.C. 154(b) by 0 days.

(21) Appl. No.: 09/150,999

(22) Filed: Sep. 10, 1998

Related U.S. Application Data

(60) Provisional application No. 60/058,585, filed on Sep. 12, 1997.

(51) Int. Cl.[7] ................................................. A61K 48/00
(52) U.S. Cl. ................................. 514/44; 800/8; 800/21
(58) Field of Search ................................. 514/44; 800/8, 800/21

(56) References Cited

U.S. PATENT DOCUMENTS

| | | | |
|---|---|---|---|
| 4,689,320 | 8/1987 | Kaji | 514/44 |
| 4,806,463 | 2/1989 | Goodchild | 435/5 |
| 5,149,797 | 9/1992 | Pederson | 536/27 |
| 5,194,428 | 3/1993 | Agrawal | 514/44 |
| 5,591,721 | 1/1997 | Agrawal et al. | 514/44 |
| 6,025,193 | * 2/2000 | Weiss | 435/320.1 |

FOREIGN PATENT DOCUMENTS

WO 9706662   2/1997   (WO) .

OTHER PUBLICATIONS

James, W. Towards Gene–Inhibition Therapy: A Review of Progress and Prospects in the Field of Antiviral Antisense Nucleic Acids and Ribozymes. Antiviral Chemistry & Chemotherapy, vol. 2, pp. 191–214, 1991.*
Roush, W. Antisense Aims for a Renaissance. Science, vol. 276, pp. 1192–1193, May 23, 1997.*
Crooke, S. T. au.,ed. Basic Principles of Antisense Therapeutics. Antisense Research and Application. Springer, Chapter 1, pp. 1–50, 1998.*
Agrawal, et al., 1988. "Oligodeoxynucleoside phosphoramidates and phosphorothioates as inhibitors of human immunodeficiency virus." Proc Natl Acad Sci USA. 85: 7079–7083.
Agrawal, et al., 1995. "Modified oligonucleotides as therapeutic and diagnostic agents." Current Opinion Biotech. 6: 12–19.
Agrawal, 1992. "Antisense oligonucleotides as antiviral agents." Trends Biotech 10: 152–158.
Agrawal, 1996. "Antisense oligonucleotides: towards clinical trials." Trends Biotechnol. 14:376–387.
Aiello, et al., 1994. "Vascular endothelial growth factor in ocular find of patients with diabetic retinopathy and other retinal disorders." New Eng J Med. 331: 1480–1487.
Anderson, 1990. "Adhesion molecules and animal development," Experimentia. 46: 2–13.

Augustine, et al., 1995. "Antisense inhibition of engrailed genes in mouse embryos reveals roles for these genes in craniofacial and neural tube development." Teratology. 51: 300–310.
Brice, et al., 1993. "Modulation of mouse preimplantation development by epidermal growth factor receptor antibodies, antisense RNA, and deoxyoligonucleotides." Dev Genet. 14: 174–184.
Cameliet, et al., 1996. "Abnormal blood vessel development and lethality in embryos lacking a single VEGF allele." Nature. 380: 435–439.
Caruthers, et al., 1987. "Chemical synthesis of deoxyoligonucleotides by the phosphoramidite method." Meth Enzymol. 154: 287–313.
Chen, et al., 1995. "Antisense oligonucleotide down–regulation of E–cadherin in the yolk sac and cranial neural tube malformations." Biol Reprod. 53: 1229–1238.
Claffey, et al., 1992. "Vascular endothelial growth factor. Regulation by cell differentiation and activated second messenger pathways." J Biol Chem. 267: 16317–16322.
Crooke, et al., 1996. "Progress in antisense oligonucleotide therapeutics." Ann Rev Pharmacol Med. 36: 107–129.
Ferrara, et al., 1997. "The biology of vascular endothelial growth factor." Endocrine Reviews. 18: 4–25.
Gaudette, et al., 1993. "Effect on embryos of injection of phosphorothioate–modified oligonucleotides into pregnant mice." Antisense Res Dev. 3: 391–397.
Kim, et al., 1993. "Inhibition of vascular endothelial growth factor–induced angiogenesis suppresses tumour growth in vivo." Nature. 362: 841–844.
Kitamoto, et al., 1997. "Vascular endothelial growth factor is an essential molecule for mouse kidney development: glomerulogenesis and nephrogenesis." J Clin Invest. 99: 2351–7.
Mansour, 1990. "Gene targeting in murine embryonic stem cells: introduction of specific alterations into the mammalian genome." Genet Anal Tech App. 7: 219–227.
Monia, et al., 1996. "Antitumor activity of a phosphorothioate antisense oligodeoxynucleotide targeted against C–raf kinase." Nature Medicine. 2: 668–675.
Ochiya et al., 1995. "Hst–1 (FGF–4) antisense oligonucleotides block murine limb development." J Cell Biol. 130: 997–1003.
Plate, et al., 1992. "Vascular endothelial growth factor is a potential tumour angiogenesis factor in human gliomas in vivo." 359: 845–848.

(List continued on next page.)

Primary Examiner—Scott D. Priebe
(74) Attorney, Agent, or Firm—Hale and Dorr LLP

(57) ABSTRACT

This invention provides synthetic oligonucleotides that are useful for transplacental delivery, the oligonucleotides being DNA or RNA or both, preferably between 12–35 nucleotides in length, having a stabilized and charged backbone and at least one chemically modified base or sugar moiety, wherein the modified base or sugar moiety facilitates transplacental delivery.

10 Claims, 3 Drawing Sheets

OTHER PUBLICATIONS

Robertson, 1991. "Using embryonic stem cells to introduce mutations into the mouse germ line." Biol Reprod. 44: 238–245.

Senger, et al., 1986. "A highly conserved vascular permeability factor secreted by a variety of human and rodent tumor cell lines." Cancer Res. 46:5629–5632.

Shweiki, et al., 1992. "Vascular endothelial growth factor induced by hypoxia may mediate hypoxia–initiated angiogenesis." Nature. 359: 843–845.

Stein, et al., 1993. "Antisense oligonucleotides as therapeutic agents—is the bullet really magical?" Science. 261: 1004–1012.

Storey, et al., 1991. "Anti–sense phosphorothioate oligonucleotides have both specific and non–specific effects on cells containing human papilloma virus type 16." Nucleic Acids Res. 19: 4109–4114.

Stutz, et al., 1997. "In vivo antisense oligodeoxynucleotide mapping reveals masked regulatory elements in an mRNA dormant in mouse oocytes." Mol Cell Biol. 17: 1759–1767.

Takeichi, et al., 1998. "The cadherins: cell–cell adhesion molecules controlling animal morphogenesis." Development. 102: 639–655.

Tang, et al., 1993. "Self–stabilized antisense oligodeoxynucleotide phosphorothioates: properties and anti–HIV activity." Nucleic Acids Res. 20: 2729–2735.

Tischer, et al., 1991 "The human gene for vascular endothelial growth factor. Multiple protein forms are encoded through alternative exon splicing." J Biol Chem. 266: 11947–11954.

Wagner, 1994. "Gene inhibition using antisense oligodeoxynucleotides." Nature. 372: 333–335.

Zimmer, 1992. "Manipulating the genome by homologous recombination in embryonic stem cells." Ann Rev Neurosci. 15: 115–137.

* cited by examiner

Vm:      5'- CAG CCT GGC TCA CCG CCT TGG - 3'
Vm mm:   5'- CAA CTT AGC TTA CCG CCT TAG - 3'

M3:      5'- TCG CGC TCC CTC TCT CCG GC - 3'
M3 mm:   5'- TCA CGT TCC TTC TCC CCA GC - 3'

M13:     5'- CGC TCC CTC TCT CCG GCT CG - 3'
M13 mm:  5'- CGT TCT CTC CCT CCA GCC CG - 3'

H3:      5'- CAC CCA AGA CAG CAG AAA G - 3'
H3mm:    5'- CAT CCG AGG CAA CAA AAA G - 3'

E-cad:    5'- GGA AAA GCT GCG GCA CCG - 3'
E-cad mm: 5'- GGA CAA GAT CCG GCA GCG - 3'

Vm dose response

| Dose (mg/kg) | Activity (E8) | # Litters | Activity (E17) | # Litters |
|---|---|---|---|---|
| 25 | + | 16 | + | 10 |
| 18 | + | 46 | + | 9 |
| 15 | +/− | 4/2 | − | 6 |
| 12 | − | 5 | − | 6 |
| 6 | − | 7 | ND | 0 |
| 1 | − | 3 | ND | 0 |

FIG. 3

TRANSPLACENTAL DELIVERY OF OLIGONUCLEOTIDES

CROSS-REFERENCE TO RELATED APPLICATIONS

This application is a U.S. Utility Patent Application which claims priority from U.S. Provisional Patent Application Ser. No. 60/058,585, filed on Sep. 12, 1997.

FIELD OF THE INVENTION

This invention relates to the modulation of gene expression in embryos via the transplacental delivery of oligonucleotides. This invention also relates to methods of determining the function of a gene using non-human mammalian gene knockout models produced via transplacental delivery of oligonucleotides to non-human mammalian embryos.

BACKGROUND OF THE INVENTION

With the rapidly growing database of gene sequence information, there is a need for techniques that can rapidly and efficiently attribute function in vivo. To date, in a mammalian model, the only solution has been the generation of transgenic knockout animals. Knockout animal models such as mice and rats are a powerful tool in studying the role genes play during development. In these models, a targeted gene is made non-functional, resulting in an altered phenotype. This phenotype may be indicative of the function of the gene and the role it plays during development. However, the transgenic knockout method suffers from several significant drawbacks, including technical difficulty, time required, the limitation to single gene targets, and the inability to uncover time-dependent secondary phenotypes.

Currently, the most widely used approach in which such knockouts are created is disruption of the gene by genetic recombination with exogenous DNA (Mansour (1990) *Genet. Anal. Tech. App.* 7:219–227; Robertson (1991) *Biol. Reprod.* 44:238–245; Zimmer (1992) *Ann. Rev. Neurosci.* 15:115–137). In this process oocytes collected from an animal stimulated to superovulate are transfected with the exogenous DNA. Recombination occurs, resulting in an oocyte with a non-functional gene. The oocyte is then fertilized, and implanted back into the animal. All subsequent progeny of these transformed animals will contain a disrupted target gene. However, this procedure suffers from several significant drawbacks. The transgenic knockout method is expensive, complex, and time consuming. In addition, the recombination event is limited to a point early in development. Finally, the technique is not capable of targeting more than one gene at a time, except as mating events between the eventual progeny of two separate recombination knockout animals.

Another method which has been used to create animal knockouts is the treatment of embryos in vitro with antisense RNA (Brice et al. (1993) *Dev. Genet* 14:174–184) or DNA (Brice et al. (1993) *Dev. Genet.* 14:174–184; Ochiya et al. (1995) *J CellBiol.* 130:997–1003; Chen et al. (1995) *Biol. Reprod.* 53:1229–1238; Augustine et al. (1995) *Teratol.* 51:300–310; Stutz et al. (1997) *Mol. Cell. Biol.* 17:1759–1767). Antisense approaches have the advantage of disrupting gene expression at the level of mRNA, resulting in the equivalent of a homozygous knockout phenotype. However, the methodology currently used is also expensive, complex, and time-consuming, in that it requires manipulation and growth of embryos in an artificial in vitro environment. It would be a distinct advantage to be able to administer oligonucleotides to pregnant mice in order to generate phenotypic knockouts directly, rather than treat embryos in vitro. The obvious barrier to this is the placenta.

Thus, improved methods of producing knockout models and of defining and studying gene function are still needed.

Antisense oligonucleotides have shown promise as candidates for therapeutic applications for diseases and disorders resulting from expression of cellular genes (see, e.g., WO 95/09236, WO 94/26887, and PCT/US/13685). Synthetic antisense oligonucleotides have also been demonstrated to be useful tools in inhibiting a wide variety of viruses (see, e.g., Agrawal (1992) *Trends Biotech.* 10: 152–158). The development of various antisense oligonucleotides as therapeutic and diagnostic agents has recently been reviewed by Agrawal and Iyer (*Current Opinion Biotech.* (1995) 6:12–19). More recently, the antisense approach has been found to be useful for therapeutic treatment in vivo (see e.g., Agrawal (1996) *TIBTECH* 14:376–387; Monia et al. (1996) *Nature Medicine* 2:668–675; Crooke et al. (1996) *Ann. Rev. Pharmacol. Med.* 36:107–129).

However, neither the treatment of embryos for viral infections or aberrant gene expression nor the modulation of embryonic genes or foreign genes harbored by embryos have heretofore been successfully accomplished in utero via the antisense approach. Such demonstrations become important when devising noninvasive therapeutic methods and informative in vivo models for human disease. It has been shown that phosphorothioate-modified oligonucleotides injected into pregnant female mice are not toxic or teratogenic to embryos in a non-specific way (Gaudette et al. (1993) *Antisense Res. Dev.* 3:391–397).

Accordingly, there remains a need for effective gene-specific antisense oligonucleotide therapy suitable for treatment in mammalian embryos.

SUMMARY OF THE INVENTION

It has been discovered that modified synthetic oligonucleotides, when administered systemically to a pregnant mammal, can pass through its placenta to an embryo in utero, where modulation of the expression of a target gene is effectuated. The ramifications of this discovery are expected to change the strategy currently used for treating infections, diseases, and disorders caused by aberrant gene-specific expression in embryos. This discovery has been exploited to develop the present invention which includes methods of modulating gene expression and of delivering intact synthetic oligonucleotides to an embryo in utero, and concomitantly, to its mother; methods and knockout models for determining gene function; and methods for producing such models.

Synthetic oligonucleotides that are useful for transplacental delivery are oligonucleotides which are DNA or RNA or both, preferably between 12–35 nucleotides in length, having a stabilized and charged backbone and at least one chemically modified base or sugar moiety, wherein the modified base or sugar moiety facilitates transplacental delivery.

As an illustration, an oligonucleotide with phosphodiester internucleotide linkages is an oligonucleotide with a non-stabilized backbone. Such constructs are not stable and are degraded in vivo. Oligonucleotides with phosphorothioate modified internucleotide linkages are stable and persist in maternal tissue. In another illustration, oligonucleotides with methyl phosphonate internucleotide linkages exemplify a non-charged oligonucleotide variant that is inactive in this system. An illustration of a successfully modified base or sugar moiety would be a 2'-O-methyl ribonucleotide.

Additional illustrations will further elucidate the invention. Oligonucleotides modified with phosphorothioate alone are stable but do not cross the placenta (Gaudette et al. (1993) *Antisense Res. Dev.* 3:391–397). Inverted chimeric oligonucleotides that are comprised of a phosphorothioate core region flanked by regions of phosphodiester at the 5' and 3' ends are not effective because their phosphodiester linkages are not sufficiently stabilized, and are degraded in vivo. A phosphorothioate backbone is charged, but needs a further modification to the base or bases to facilitate transplacental delivery. At least one 2'-O-methyl ribonucleotide is such a modification, although any 2' substitution that successfully facilitates transplacental delivery is contemplated. A preferred embodiment is a phosphorothioate oligonucleotide containing at least one 2'-O-methyl modified ribonucleotide. This preferred composition is effective as it is both stabilized and modified for transplacental uptake.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 3 is a chart indicating induction of the angiogenesis defect phenotype in a dose-dependent manner upon treatment with Vm 2'-O-methyl phosphorothioate oligonucleotide.

DETAILED DESCRIPTION OF THE PREFERRED EMBODIMENTS

Figure 1:
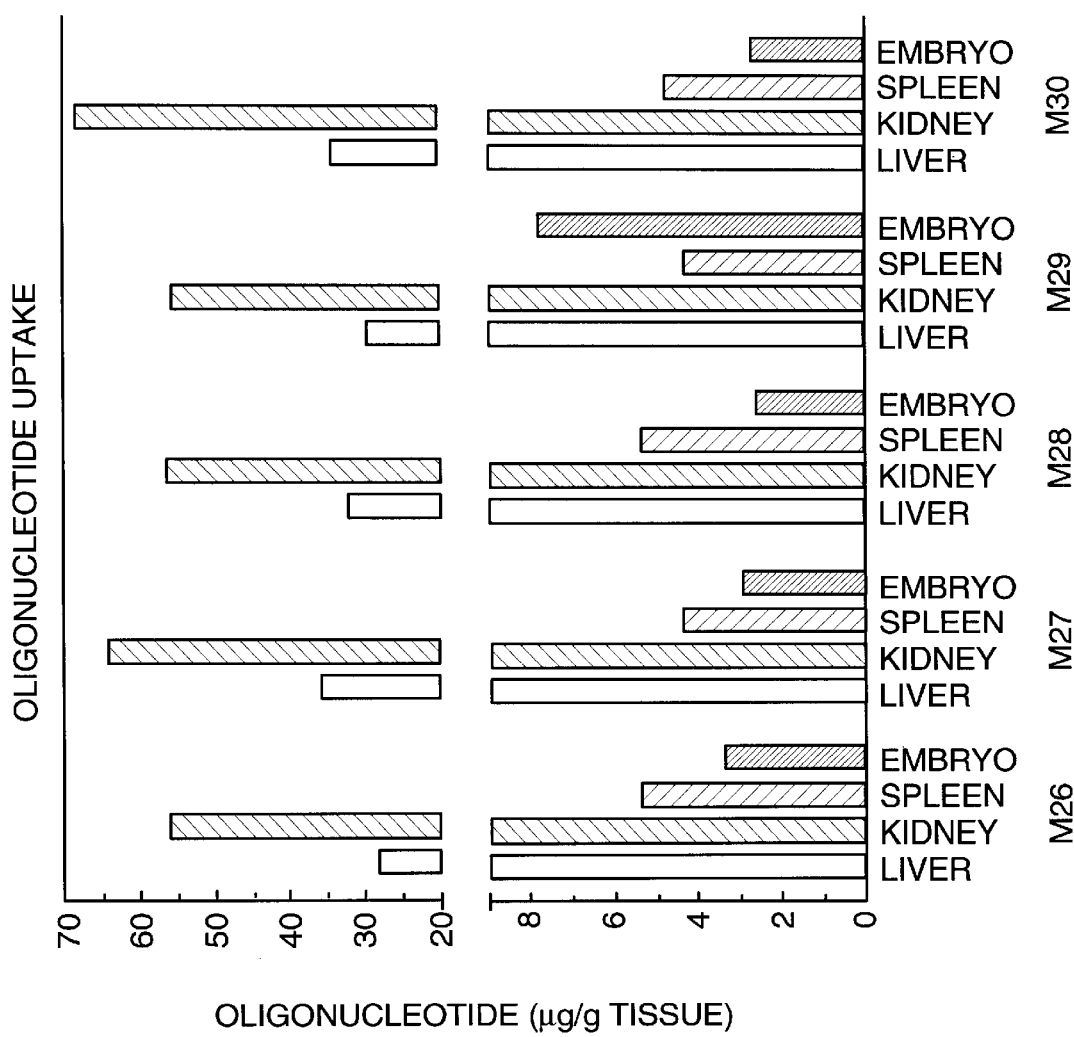
FIG. 1 is a graphic representation of synthetic oligonucleotide detected in different tissues and in the embryos of pregnant mice 48 hours after systemic administration of the oligonucleotide to the pregnant mice.

The patent and scientific literature referred to herein establishes the knowledge that is available to those with skill in the art. The issued U.S. patents, allowed applications, and references cited herein are hereby incorporated by reference. The present invention provides methods of modulating gene expression in a mammalian embryo via the transplacental delivery of oligonucleotides specific for the targeted gene to the embryo from the pregnant mammal.

Many uncharacterized sequences have been identified by genome sequencing projects. The present invention describes a technically simple gene knockout system that is oligonucleotide based and that provides a rapid, inexpensive alternative to transgenic knockout model systems for the determination of gene function and/or identification. A large scale use of this invention would allow for high-throughput screening of novel gene sequences, thus identifying potential new therapeutic targets in conjunction with providing valuable information on active antisense oligonucleotides as lead compounds in any subsequent clinical development. The invention can be performed at any time during gestation, which provides a much wider range of valid targets. Also, more types of analyses can be performed. Not all genetic information can be obtained by observing a gene's sequence outside its natural context. Ordering genes in a functional pathway (epistasis) can be analyzed in this system. Multiple knockouts can be achieved simply by dosing with more than one active oligonucleotide.

The present invention provides for the treatment of embryos in utero, e.g., for viral infections such as HIV, HSV, HBV, rubivirus, influenza, or CMV; for genetic disorders resulting from the expression of a foreign gene, such as one from a pathogen, including, but not limited to, Streptococci, *E. coli*, Listeria, Enterococci, tuberculosis, Neosseria, Gram negative enteric organisms; or from the expression of aberrant, e.g., overexpression of a normal gene. The present method is preferable to existing methods of fetal treatment, as it does not require risky physical manipulation of the embryo or any invasive procedures. In addition, the pregnant mammal can be treated concomitantly with the embryo because of the nature of the claimed method, which comprises systemic administration of the oligonucleotide to the pregnant mammal. The administered oligonucleotides cross the placenta and enter the tissues of the embryo intact, where they down-regulate or modulate the expression of the gene (s) to which they have been directed.

Down-regulation of the gene is thought to occur when the oligonucleotide which has been transplacentally administered enters the embryo and binds to a complementary single-stranded nucleic acid therein sequence according to the Watson-Crick or the Hoogsteen rule of base pairing. In doing so, the oligonucleotide disrupts the function of the target by one of several mechanisms: by preventing the binding of factors required for normal translation, splicing, or transcription; in the case of an mRNA target, by triggering the enzymatic destruction of the message by RNase H; or by destroying the target via reactive groups attached directly to the antisense oligonucleotide, thereby inhibiting splicing and translation of RNA. Antisense oligonucleotides have also been shown to bind to genomic DNA, forming a triplex, and inhibit transcription. (see generally, Agrawal (1992) *Trends in Biotech.* 10:152–158; Wagner (1994) *Nature* 372:333–335; and Stein et al. (1993) *Science* 261:1004–1012).

The oligonucleotide delivered to the embryo according to the methods of the invention are composed of ribonucleotides, deoxyribonucleotides, or a combination of both, with the 5' end of one nucleotide and the 3' end of another nucleotide being covalently linked. These oligonucleotides are at least about 12 nucleotides in length, but are preferably 15 to 35 nucleotides long, with 20 to 25 mers being the most common.

These oligonucleotides can be prepared by the art recognized methods such as phosphoramidate or H-phosphonate chemistry which can be carried out manually or by an automated synthesizer as described in Agrawal (*Trends Biotechnol.* (1992) 10: 152–158) and in Uhlmann et al. (*Chem. Rev.* (1990) 90:534–583).

In a first aspect, the invention provides a method of modulating the expression of a gene in a mammalian embryo in utero. As used herein, the term "modulating the expression" refers to (a) the inhibition or down-regulation of expression of a targeted gene or nucleic acid, or (b) activation or up-regulation of a gene or nucleic acid which expression is regulated by a targeted negative regulator or repressor. We prefer modulation by (a) the inhibition or down-regulation of expression of a targeted gene or nucleic acid. The gene being modulated can be any endogenous or exogenous gene expressed in an embryo during its development and after its birth. An "endogenous gene" refers to a gene normally found in the embryo, whereas an "exogenous gene" refers to the gene of a virus or other pathogen, e.g., bacteria, which has become associated with and later expressed in the tissues of the embryo and/or mammal after birth. The targeted gene may also be a regulator of the gene of interest.

In the method of the invention, a synthetic oligonucleotide specific for a nucleic acid is transplacentally delivered to the mammalian embryo in utero, the oligonucleotide being systemically administered to a pregnant mammal with a pharmaceutically acceptable carrier. The oligonucleotide so administered crosses the placenta and inhibits the expression of the gene in the embryo and/or mammal after birth.

The term "systemically administered" is used herein as delivery of the drug to the whole organism by oral ingestion, enteral or colorectal administration, or by intramuscular, intravenous, subcutaneous, or intraperitoneal injection. The term "nucleic acid" is meant to encompass a genomic region or an RNA molecule transcribed therefrom. In some embodiments, the nucleic acid is mRNA.

Without being limited to any theory or mechanism, it is generally believed that the activity of oligonucleotides used in accordance with this method of the invention depends on the hybridization of the oligonucleotide to the target nucleic acid (e.g. to at least a portion of a genomic region, gene or mRNA transcript thereof), thus disrupting the function of the target. Such hybridization under physiological conditions is measured as a practical matter by observing interference with the function of the nucleic acid sequence. Thus, a preferred oligonucleotide used in accordance with the invention is capable of facilitated uptake across the placenta, of forming a stable duplex (or triplex in the Hoogsteen pairing mechanism) with the target nucleic acid; of activating RNase H and thereby causing effective destruction of the target RNA molecule; and, in addition, is capable of resisting nucleolytic degradation (e.g. endonuclease and exonuclease activity) in vivo. A number of the modifications to oligonucleotides described below and others which are known in the art specifically and successfully address each of these preferred characteristics.

As used herein the term "mammal" is limited to vertebrates that bear their young live, including, but not limited to, rodents, primates, and specifically, humans. The term "non-human mammal" excludes humans from the group.

As used herein, the term "synthetic oligonucleotide" refers to chemically synthesized polymers of nucleotides covalently attached via at least one 5' to 3' internucleotide linkage. In some embodiments, these oligonucleotides contain at least one deoxyribonucleotide, ribonucleotide, or both deoxyribonucleotides and ribonucleotides. These oligonucleotides are typically from 12 to 35 nucleotides in length.

In some embodiments, the oligonucleotides may also be modified in a number of ways without compromising their ability to hybridize to nucleotide sequences contained within the targeted mRNA. The term "modified synthetic oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. In some embodiments, at least one internucleotide linkage of the oligonucleotide is an alkylphosphonate, phosphorothioate, phosphorodithioate, alkylphosphonothioate, phosphoramidate, carbamate, carbonate, phosphate triester, and/or acetamidate. In some preferred embodiments, the nucleotides of the synthetic oligonucleotides are linked by one or at least one phosphorothioate internucleotide linkage. The phosphorothioate linkages may be mixed $R_p$ and $S_p$ enantiomers, or they may be stereoregular or substantially stereoregular in either $R_p$ or $S_p$ form (see Iyer et al. (1995) Tetrahedron Asymmetry 6:1051–1054). In one particular embodiment, the internucleotide linkages in the oligonucleotide used in the methods of the invention are each linked via phosphorothioate internucleotide linkages.

Modified oligonucleotides also may be "chimeric" in that they have more than one type of internucleotide linkage. For example, U.S. Pat. No. 5,149,797 describes traditional chimeric oligonucleotides having a phosphorothioate core region interposed between methylphosphonate or phosphoramidate flanking regions. PCT Application No. PCT US596/13371, filed on Aug. 16, 1996, discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate.

In addition, the term "modified oligonucleotide" encompasses oligonucleotides with a modified base and/or sugar. In addition, unoxidized or partially oxidized oligonucleotides having a substitution in one nonbridging oxygen per nucleotide in the molecule are considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention. Other modifications include those which are internal or are at the end(s) of the oligonucleotide molecule and include additions to the molecule of the internucleoside phosphate linkages, and terminal ribose, deoxyribose and phosphate modifications which cleave, or crosslink to the opposite chains or to associated enzymes or other proteins which bind to the genome or RNA.

The term "modified oligonucleotide" also encompasses oligonucleotides having at least one nucleotide with a modified base and/or sugar, such as a 2'-O-substituted ribonucleotide. For purposes of the invention, the term "2'-O-substituted" means substitution of the 2' position of the pentose moiety with an -O- lower alkyl group containing 1–6 saturated or unsaturated carbon atoms, or with an -O-aryl or -allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. In some embodiments the oligonucleotides of the invention include two or four ribonucleotides 2'-O-alkylated at their 5'terminus (i.e., 5'2-O-alkylated ribonucleotides), and/or two or four ribonucleotides 2'-O-alkylated at their 3' terminus (i.e., 3'2-O-alkylated ribonucleotides). In some preferred embodiments, the oligonucleotide is a 2'-O-methylated hybrid oligonucleotide.

The invention also provides for the modification of synthetic oligonucleotides so as to facilitate their uptake across the placenta. Modifications include, but are not limited to, the presence of a stabilized backbone. Modifications further include the presence of a charged backbone. Modifications also include a chemically modified base or sugar moiety, wherein said moiety successfully facilitates transplacental uptake and delivery. As an illustration, an oligonucleotide with phosphodiester internucleotide linkages is an oligonucleotide with a non-stabilized backbone. Such constructs are not stable and are degraded in vivo. Oligonucleotides with phosphorothioate modified internucleotide linkages are stable and persist in maternal tissue. In another illustration, oligonucleotides with methyl phosphonate internucleotide linkages exemplify a non-charged oligonucleotide variant that is inactive in this system. An illustration of a successfully modified base or sugar moiety would be a 2'-O-methyl ribonucleotide.

Additional examples will further elucidate the invention. Oligonucleotides modified with phosphorothioate alone are stable but do not cross the placenta (Gaudette et al. (1993) *Antisense Res. Dev.* 3:391–397). Inverted chimeric oligonucleotides that are comprised of a phosphorothioate core region flanked by regions of phosphodiester at the 5' and 3' ends are not effective because their phosphodiester linkages are not sufficiently stabilized and are degraded in vivo. A phosphorothioate backbone is charged, but needs a further modification to the base or bases to facilitate transplacental delivery. Al least one 2'-O-methyl ribonucleotide is such a modification, although any 2' substitution that successfully facilitates transplacental delivery is contemplated. A preferred embodiment is a phosphorothioate oligonucleotide containing at least one 2'-O-methyl modified ribonucleotide. This preferred composition is effective as it is both stabilized and modified for transplacental uptake.

In another aspect, the invention provides a method of determining the function of a gene expressed in a mammal. In this method, a chemically modified synthetic oligonucleotide specific for the gene is transplacentally delivered to a non-human mammalian embryo by systemically administering the oligonucleotide in a pharmaceutically acceptable carrier to a pregnant non-human mammal. The oligonucleotide inhibits the expression of the gene, thereby altering the phenotype of the embryo and possibly the mammal after birth. The altered phenotype of the embryo and/or mammal would be indicative of the function of the gene.

The present method also provides a phenotypic knockout model, comprising an embryo in a pregnant, non-human mammal to which has been transplacentally administered in utero a synthetic oligonucleotide specific for a gene expressed in the embryo or in the mammal after birth, the oligonucleotide modulating the expression of the gene, thereby resulting in an altered phenotype. In another aspect, the invention provides a method of transplacentally delivering a synthetic oligonucleotide to a mammalian embryo. In this method, the synthetic oligonucleotide and a pharmaceutically acceptable carrier are systemically administered to a pregnant mammal. The oligonucleotide passes through the placenta into the embryo.

In some embodiments, the oligonucleotide has modified internucleotide linkages. In certain embodiments, the oligonucleotide has phosphorothioate internucleotide linkages. In preferred embodiments, the oligonucleotide further comprises at least one 2'-O-substituted ribonucleotide. In particular embodiments, the 2'-O-substituted ribonucleotide is a 2'-O-alkyl ribonucleotide such as a 2'-O-methyl ribonucleotide. In preferred embodiments, the oligonucleotide further comprises at least one 2'-O-substituted ribonucleotide at its 3' terminus and at least one 2'-O-substituted ribonucleotide at its 5' terminus. In other preferred embodiments, the oligonucleotide comprises at least two 2'-O-substituted ribonucleotides at its 3' terminus and at least two 2'-O-substituted ribonucleotides at its 5' terminus. In particular embodiments, the oligonucleotide further comprises four 2'-O-substituted ribonucleotides at its 3' terminus and four 2'-O substituted ribonucleotides at its 5' terminus (i.e., a "4×4 hybrid").

The invention also provides a method of delivering a synthetic oligonucleotide to a mammalian embryo, comprising systemically administering to a pregnant mammal the oligonucleotide and a pharmaceutically acceptable carrier, wherein the oligonucleotide passes through the placenta into the fetus in intact form. "Intact form" is used herein to mean undigested by nucleases or partially digested but still functional as an antisense oligonucleotide in its ability to modulate gene expression. For example, a pro-drug is designed to be partially digested in vivo to obtain its intact active form.

It is preferable that the oligonucleotides used according to the methods of the invention be modified so as to reduce chances of their degradation by nucleases. Any modification is allowable as long as it is not non-specifically toxic to the mammal. However, for oligonucleotides used in the method of modulating gene expression, this modification must not compromise their ability to hybridize to the target nucleic acid. One type of modification is the presence of other than phosphodiester internucleotide linkages between the 5' end of one nucleotide and the 3' end of another nucleotide in which the 5' nucleotide phosphodiester linkage has been replaced with any number of chemical groups. Examples of such chemical groups include alkylphosphonates, phosphorothioates, phosphorodithioates, alkylphosphonothioates, phosphoramidates, carbamates, acetamidate, carbonates, and phosphate triesters.

Preferred internucleotide linkages are phosphorothioates. Phosphorothioate internucleotide linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051–1054). Oligonucleotides with phosphorothioate linkages can be prepared using methods well known in the field such as phosphoramidite (see, e.g., Agrawal et al. (1988) *Proc. Natl. Acad. Sci. (USA)* 85:7079–7083) or by H-phosphonate (see, e.g., Froehler (1986) *Tetrahedron Lett.* 27:5575–5578) chemistry. The synthetic methods described in Bergot et al. (*J Chromatog* (1992) 559:35–42) can also be used.

Modified oligonucleotides also may be "chimeric" in that they have more than one type of internucleotide linkage. For example, U.S. Pat. No. 5,149,797 describes traditional chimeric oligonucleotides having a phosphorothioate core region interposed between methylphosphonate or phosphoramidate flanking regions. PCT Application No. PCT US596/13371, filed on Aug. 16, 1996, discloses "inverted" chimeric oligonucleotides comprising one or more nonionic oligonucleotide region(s) (e.g. alkylphosphonate and/or phosphoramidate and/or phosphotriester internucleoside linkage) flanked by one or more region(s) of oligonucleotide phosphorothioate.

Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide.

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3',5'-substituted oligonucleotide having a sugar which, at both its 3' and 5' positions is attached to a chemical group other than a hydroxyl group (at its 3' position) and other than a phosphate group (at its 5' position).

Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

Preferred modified oligonucleotides used in the methods of the invention are hybrid oligonucleotides containing both deoxyribonucleotides and at least one ribonucleotide. Preferably the modified oligonucleotides contain at least two 2' substituted ribonucleotides at their termin(i/us). For purposes of the invention, the term "2' substituted" means substitution at the 2' position of the ribose with, e.g., an -O-lower alkyl containing 1–6 carbon atoms, aryl or substituted aryl or allyl having 2–6 carbon atoms e.g., 2'-O-allyl, 2'-O-aryl, 2'-O-alkyl, 2'-halo, or 2'-O-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups. Useful substituted ribonucleotides are 2'-O-alkyls such as 2'-O-methyl, 2'-O-ethyl, 2'-O-propyl, with 2'-O-methyl being the most preferred.

The hybrid oligonucleotides useful in the method of the invention resist nucleolytic degradation, form stable duplexes with RNA or DNA, and preferably activate RNase H when hybridized with RNA. They may additionally include at least one unsubstituted ribonucleotide. For example, an oligonucleotide useful in the method of the invention may contain all deoxyribonucleotides with the exception of two 2' substituted ribonucleotides at the 3' terminus of the oligonucleotide, or the 5' terminus of the oligonucleotide. Alternatively, the oligonucleotide may have at least two, and preferably four, substituted ribonucleotides at both its 3' and 5' termini.

The preparation of modified oligonucleotides is well known in the art (reviewed in Agrawal (1992) *Trends Biotechnol.* 10:152–158; Agrawal et al. (1995) *Curr. Opin. Biotechnol* 6:12–19; see also Goodchild (1990) *Bioconjugate Chem.* 2:165–187; Agrawal et al., (1988) *Proc. Nail. Acad. Sci.* (USA) 85:7079–7083; and Uhlmann et al. (1990) *Chem. Rev.* 90:534–583). For example, nucleotides can be covalently linked using art-recognized techniques such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron. Lett.* 28: (31):3539–3542); Caruthers et al. (1987) *Meth. Enzymol.* 154:287–313; U.S. Pat. No. 5,149,798). Oligomeric phosphorothioate analogs can be prepared using methods well known in the field such as methoxyphosphoramidite (see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

The oligonucleotides transplacentally delivered to the embryo intact can have any desired nucleotide sequence. In the method of modulating gene expression in an embryo, the oligonucleotide administered has a nucleotide sequence which is complementary to an exogenous or endogenous gene expressed at some gestational time in the embryo. Useful nucleotide sequences include those complementary to nucleic acids from viruses or other pathogens infecting the embryo and/or the pregnant mother, and to normal or aberrant genes or mRNAs normally or aberrantly expressed in the embryo.

For purposes of the invention, the term "oligonucleotide sequence that is complementary to a nucleic acid sequence" is intended to mean an oligonucleotide sequence that binds to the target nucleic acid sequence under physiological conditions, e.g., by Watson-Crick base pairing (interaction between oligonucleotide and single stranded nucleic acid) or by Hoogsteen base pairing (interaction between oligonucleotide and double-stranded nucleic acid) or by any other means including in the case of a oligonucleotide binding to RNA, pseudoknot formation. Such binding (by Watson Crick base pairing) under physiological conditions is measured as a practical matter by observing interference with the function of the nucleic acid sequence.

The sequence of the nucleic acid that is complementary to an oligonucleotide used according to the methods of the invention will vary, depending upon the gene to be modulated or down-regulated. In some cases, the gene or nucleic acid sequence targeted by the oligonucleotide will be a virus nucleic acid sequence. The use of antisense oligonucleotides to inhibit various viruses is well known (reviewed in Agrawal (1992) *Trends in Biotech.* 10:152–158). Viral nucleic acid sequences that are complementary to effective antisense oligonucleotides have been described for many viruses, including human immunodeficiency virus type 1 (HIV-1) (U.S. Pat. No. 4,806,463), herpes simplex virus (U.S. Pat. No. 4,689,320), influenza virus (U.S. Pat. No. 5,194,428), and human papilloma virus (Storey et al. (1991) *Nucleic Acids Res.* 19:4109–4114). Sequences complementary to any of these nucleic acid sequences can be used for oligonucleotides according to the invention, as can be oligonucleotide sequences complementary to nucleic acid sequences from any other virus which could infect the embryo in utero.

Other oligonucleotides used in the method according to the invention can have a nucleotide sequence complementary to a cellular gene or gene transcript, the abnormal expression or product of which results in a disease state. The nucleic acid sequences of several such cellular genes have been described, including prion protein (Stahl et al. (1991) *FASEB J.* 5:2799–2807), the amyloid-like protein associated with Alzheimer's disease (U.S. Pat. No. 5,015,570), and various well-known oncogenes and proto-oncogenes, such as c-myb, c-myc, c-abl, and N-ras. In addition, oligonucleotides that inhibit the synthesis of structural proteins or enzymes involved largely or exclusively in oogenesis, spermatogenesis, sperm motility, or sperm viability may be useful. Hypertension may be controlled by oligonucleotides that down-regulate the synthesis of angiotensin converting enzyme or related enzymes in the renin/angiotensin system. Platelet aggregation may be controlled by suppression of the synthesis of enzymes necessary for the synthesis of thromboxane A2 for use in myocardial and cerebral circulatory disorders, infarcts, arteriosclerosis, embolism and thrombosis. Inhibition of the synthesis of cholinephosphotransferase may be useful in hypolipidemia. Hybridization arrest also may be used to reduce or eliminate adverse effects of numerous neural disorders. Suppression of selected enzymes in the arachidonic acid cascade which leads to prostaglandins and leukotrienes may be useful in the control of platelet aggregation, allergy, inflammation, pain and asthma. Suppression of the protein expressed by the multidrug resistance (mdr-1) gene, which can be responsible for development of resistance of tumors to a variety of anti-cancer drugs and is a major impediment in chemotherapy may prove to be beneficial in the treatment of cancer. Oligonucleotide sequences complementary to nucleic acid sequences from any of these genes can be used for oligonucleotides according to the methods of the invention, as can be oligonucleotide sequences complementary to any other cellular gene transcript, the abnormal expression or product of which results in a disorder or disease state.

It is not necessary that the identity or function of the gene or nucleic acid being targeted be well characterized or even known, as the method of the invention is also useful for determining the function of uncharacterized genes, for example, during development, as described below.

In the present method transplacental delivery of the oligonucleotide to the embryo in utero is accomplished via systemic administration of the oligonucleotide to the pregnant mammal carrying the embryo. The term "systemic administration" is meant to encompass delivery of the drug to the whole organism by oral ingestion, enteral or colorectal administration or by intramuscular, intravenous, subcutaneous, or intraperitoneal injection. Systemic administration to the pregnant mammal may be bolus, intermittent, or continuous, depending on the condition and response, as determined by those with skill in the art.

At least one synthetic oligonucleotide specific for at least one portion of at least one targeted gene administered according to the method of the invention may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which are able to pass through the placenta, enhance modulation of gene expression, and thus alter the function of the gene in the embryo. Such additional factors and/or agents may be administered with the oligonucleotide in the pharmaceutical composition to produce a synergistic effect or to minimize side-effects caused by the synthetic oligonucleotide. Combinations of synthetic oligonucleotides, each of which is directed to different regions of the same or different gene(s) or mRNA(s), may be used in the pharmaceutical composition administered according to the method of the invention.

One type of pharmaceutical composition may take the form of a liposome in which the synthetic oligonucleotides are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include compounds such as cyclodextrins and the like which enhance delivery of oligonucleotides into cells, as described by Zhao et al. (*Biochem. Pharmacol.* (1996) 52:1537–1544), or slow release polymers.

When a synthetic oligonucleotide is administered orally, the synthetic oligonucleotide will be in the form of a tablet, capsule, powder, solution or elixir. Then administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. Then administered in liquid form, the pharmaceutical composition contains from about 0.5% to 90% by weight of the synthetic oligonucleotide and preferably from about 1 to 50% synthetic oligonucleotide.

When the synthetic oligonucleotide of the invention is administered by intravenous, subcutaneous, intramuscular, or intraperitoneal injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, or intraperitoneal injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

When administered colorectally, the oligonucleotide as described above is delivered with a physiologically acceptable carrier, such as an inert diluent or an assimilable carrier. Suitable formulations that include pharmaceutically acceptable excipients for introducing compounds to the bloodstream by other than injection routes can be found in *Remington 's Pharmaceutical Sciences* (18th ed.) (Genarro, ed. (1990) Mack Publishing Co., Easton, Pa.). The pharmaceutical formulation that may be introduced in a solid, semi-solid, suspension, or emulsion form and may be compounded with any number of well-known, pharmaceutically acceptable additives. The oligonucleotide and other ingredients may be enclosed in a hard or soft shell gelatin capsule, contained within gels or creams, or compressed into suppositories, and the like. Sustained release delivery systems and/or coatings for colorectally administered dosage forms are also contemplated, such as those described in U.S. Pat. Nos. 4,704,295, 4,556,552, 4,309,404, and 4,309,406.

As used herein, the term "therapeutically effective amount" means the total amount of each active oligonucleotide administered that is sufficient to show a meaningful benefit to the embryo before and/or after birth, or to both the embryo and mother. For example, a therapeutically effective amount of oligonucleotide would be that amount which will reduce or eradicate detectable viral load in a neonate born to a mother with AIDS or other viral infection known to be transmittable to embryos from the mother, and in the mother. Of course, what is a therapeutically effective amount for the embryo may be different than what a therapeutically effect amount for the mother.

The amount of synthetic oligonucleotide in the pharmaceutical composition of the present invention will depend upon the nature and severity of the condition being treated in the embryo, or in the mother and embryo, and perhaps on the nature of prior treatments which the mother has undergone. Ultimately, the attending physician will decide the amount of synthetic oligonucleotide with which to treat the embryo or embryo and mother. Initially, the attending physician will administer low doses of the synthetic oligonucleotide and observe the patients' response. It is contemplated that for systemic administration (e.g., intravenous, subcutaneous, oral, or colorectal) the dosages of the pharmaceutical compositions administered in the method of the present invention should provide a total dose of about 0.1 to 10.0 mg/kg, preferably about 0.1 to 5.0 mg/kg body weight, and preferably 0.5 to 2.0 mg/kg body weight. Then administered systemically, the therapeutic composition is preferably administered at a sufficient dosage to attain a blood level of oligonucleotide from about 0.01 µM to about 10 µM. Preferably, the concentration of oligonucleotide at the site of aberrant gene expression should be from about 0.01 µM to about 10 µM, and most preferably from about 0.05 µM to about 5 µM.

The duration of systemic administration will vary, depending on the severity of the disease being treated and the condition and potential idiosyncratic response of each individual patient. Ultimately the attending physician will decide on the appropriate duration of intravenous therapy using the pharmaceutical composition of the present invention.

The present invention also provides methods of introducing an intact synthetic oligonucleotide into a mammalian embryo via the transplacental delivery of the oligonucleotide from the pregnant mammal. This method comprises the use of synthetic oligonucleotides that contain modifications comprising, but not limited to, a stabilized backbone, a charged backbone, and a chemically modified base and/or sugar moiety, wherein said moiety successfully facilitates the transplacental uptake and delivery of said, modified oligonucleotide. That the oligonucleotide is intact can be determined by sampling embryonic tissues and determining the size and sequence of the oligonucleotides by HPLC or any known method (see, e.g., U.S. Pat. No. 5,627,277, PCT/US95/01048, and PCT/US96/20266).

To determine if synthetic oligonucleotides systemically administered to a pregnant mammal can be transplacentally delivered to the embryos according to the method of the invention, and if so, if such oligonucleotides can modulate gene expression in the embryo in utero, the following study was performed. Oligonucleotides specific for vascular endothelial growth factor (VEGF), were systemically administered to pregnant mice. Forty-eight hours later, samples of various body tissues were analyzed for oligonucleotide content by anion exchange HPLC and UV absorbance.

FIG. 1 illustrates the concentration of VEGF specific hybrid oligonucleotide in the liver, kidney, spleen, and fetuses of the treated pregnant mice. Low levels of oligonucleotide are seen in the embryos from all pregnant mice analyzed. These results demonstrate that the synthetic oligonucleotide can be transplacentally delivered from the mother through the placental into the fetus.

VEGF is an endothelial cell-specific mitogen. Nucleic acid sequences encoding three forms of VEGF have been reported in humans (Tischer et al. (1991) *J. Biol. Chem.* 266:11947–11954), and comparisons between the human and the murine VEGF have revealed greater than 85% interspecies conservation (Claffey et al. (1992) *J. Biol. Chem.* 267:16317–16322). VEGF expression has recently been shown to be stimulated by hypoxia and required for tumor angiogenesis (Senger et al. (1986) *Cancer* 46:5629–5632; Kim et al. (1993) *Nature* 362:841–844; Schweiki et al. (1992) *Nature* 359:843–845; Plate et al. (1992) *Nature* 359:845–848; Tischer et al. (1994) *J. Biol. Chem.* 266:11947–11954) and retinal neovascularization (Aiello et al. (1994) *New Eng. J. Med.* 331:1480–1487). Furthermore, elevated levels of VEGF have recently been found in vitreous from patients with diabetes (Aiello et al., ibid.). Thus, regulation of VEGF expression in tissues affected by the various conditions described above could therefore be key in treatment or preventative therapies associated with hypoxia.

The primary loss of function of VEGF in the embryo has been well-characterized (Ferrara and Davis-Smith (1997) *Endocrine Reviews* 18:4–25; Carmeliet et al. (1996) *Nature* 380:435–439). Both the heterozygous and homozygous recombinant knockout phenotypes are lethal by E10.5 from a failure in primary angiogenesis. These embryos show a marked lack of vascular development and a resultant developmental arrest. Proliferation of vessels does not occur, yolk sac vessels are not apparent and embryonic development and growth are diminished. Dose response experiments in vivo are impossible with these strains because VEGF is haploinsufficient.

To determine whether synthetic oligonucleotides delivered transplacentally are able to modulate gene expression in the embryo in utero, the physical characteristics, i.e., phenotype, of the embryos after treatment were examined. All the embryos from animals treated with the chemistry control oligonucleotide appeared normal, including animals that were allowed to go to term. In animals treated with the VEGF oligonucleotide (SEQ ID NO:2) several phenotypes previously reported for murine VEGF knockout animals were observed: developmentally arrested embryos which were uniformly smaller than those from controls; embryos with anterior cranial facial deformities; and embryos with limited disorganized vascularization. The epithelium of the aorta of these animals also was highly disorganized. In addition, it was noted that animals treated with the active oligonucleotide (SEQ ID NO:2) had higher pregnancy failure than those treated with the control oligonucleotide (25% pregnant compared to 75% pregnant). This may be that, because the embryos were developmentally arrested, they died and were resorbed in these animals.

Figures 2A, 2B, 2C:
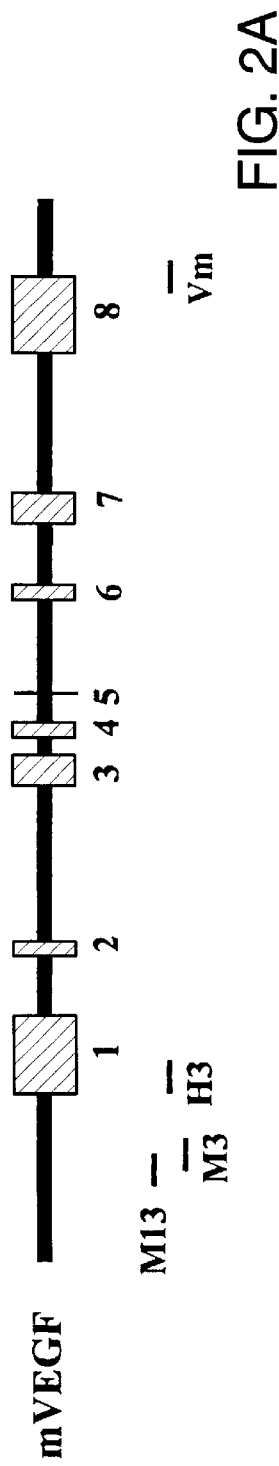
FIG. 2. (A) is a schematic of the mouse VEGF gene locus indicating the location of the synthetic modified antisense oligonucleotides used in the Examples. (B) gives the sequences of the mouse anti-VEGF specific antisense oligonucleotides and their respective mismatch (-mm) negative controls. (C) gives the sequence of the mouse anti-E-cadherin specific antisense oligonucleotide and its respective mismatch (-mm) negative control.

To assess the gene-specificity of oligonucleotide based inhibition for a second gene, E-cadherin was tested. The loss of function of E-cadherin has been characterized (Takeichi, 1988, Anderson, 1990). It had previously been shown that synthetic antisense oligonucleotides generated and introduced by amniotic microinjection into E10 embryos in culture resulted in a neural tube defect in E12 embryos (Chen, B. and Hales, B. F. (1995) *Biology of Reproduction*, 53: 1229–1238). Pregnant adult mice were treated at E10 with the E-cadherin antisense oligonucleotide (FIG. 2) according to the method of the invention and the embryos were harvested at E12.5. Each of the phenotypes described previously was identified. The principle effects were rhombencephalon edema (swollen hindbrain), neural tube closure defects and developmental arrest. The 5 bp mismatch control oligonucleotides had no effect in the embryos (FIG. 2). This same neural tube defect was observed using oligonucleotide based inhibition to E-cadherin in utero. Importantly, the developmental defects defined by oligonucleotide based inhibition of E-cadherin are separate and distinct from those defined by oligonucleotide based inhibition of VEGF.

The results supra demonstrate that oligonucleotide-based inhibition of gene expression is a powerful new tool for defining timed gene function in a mammalian model. The primary loss of function phenotype of VEGF and E-cadherin were identical to the knockout phenotype and, in addition, a secondary phenotype of VEGF was uncovered. The E-cadherin secondary phenotype (neural tube defect) had been described using antisense in embryo culture, but now has been verified in vivo. This allows narrow time ranges to be tested for inhibition, allowing the separation of phenotypes based on developmental time, which allows the generation of secondary phenotypes rapidly and easily. Recombinant transgenic knockout phenotypes in developing embryos were recapitulated at a fraction of the cost and in days instead of years.

These results confirm that sequence-specific down-regulation of gene expression in a mammalian embryo can be accomplished by transplacental administration of oligonucleotides.

In addition, a phenotypic knockout model has been developed which demonstrates that the concentration of oligonucleotides transplacentally delivered to anin the developing embryo is sufficient to inhibit development by disrupting gene expression (FIG. 3).

The present invention also provides nonhuman, mammalian knockout models for examining the function of endogenous or exogenous genes expressed in an embryo in utero. In this phenotypic model an embryo in a pregnant, nonhuman, mammal is transplacentally administered in utero a synthetic oligonucleotide specific for a gene expressed in the embryo. It is contemplated that the dosages administered in the method of the present invention should provide a total dose of about 0.1 to 100.0 mg/kg, preferably about 1 to 50 mg/kg body weight, and most preferably 18 mg/kg body weight. The oligonucleotide modulates the expression of the gene, thereby resulting in an altered phenotype in the embryo or in the mammal after it is born. In this way, the function of various genes can be determined.

This knockout model of the invention provides a solution to many of the problems of recombination knockout models. The experiments are technically simple, involving systemic administration into a pregnant adult. The return time is ordered in days rather than years, and has the potential to be far less expensive. Transplacental delivery of the oligonucleotides can be performed at any time during gestation, which provides a much wider range of valid targets and more types of analyses can be performed than in recombination knockout models. In addition, multiple knockouts can be achieved simply by dosing with more than one active oligonucleotide. Using such a combinatorial approach, large numbers of oligonucleotide sequences and gene targets can be tested for function. With this functional data, cell culture and animal models can be specifically developed to suit varied scientific and medical needs. This type of screening offers the advantage of producing not only functional information about potential new therapeutic targets, but also providing an active antisense oligonucleotide as a lead compound on any subsequent clinical development.

Additional applications for this model include epigenetic and epistatic studies. Not all genetic information can be obtained by observing the sequence of a gene outside its natural context. Ordering genes in a functional pathway (epistasis) is an important component of identifying therapeutic targets. In addition, a great deal of information is stored in structural form, and is not dependent on the linear DNA sequence. This information is largely inaccessible using other methods of genetic knockout, but can be analyzed in the oligonucleotide-based knockout models of the invention. Also, β-catenin, a member of the wingless signaling pathway in Xenopus development can be investigated as a potential new target for therapeutic applications using this model. Its role as an oncogene is well known. The investigation of p300, a histone de-acetylase, may also provide insight into diseases of imprinting. The p300 transcription factor is required for all activated transcription in cells and is a member of a dynamic epigenetic control mechanism.

The model of the invention can also be used in oligonucleotide optimization. One of the major areas of optimization of active oligonucleotides is in the variant chemistries. Modifications to every portion of the molecule have been tested, but the assays for function have remained in tissue culture. This in vivo model for function significantly enhance the relevance of any optimization procedure. In addition, establishing the present model system that can test the interaction of oligonucleotides and targets in a normal in vivo setting will provide invaluable data about the accessibility of certain target sequences. These data can be compiled into a database that will correlate function with sequence motifs, to dramatically enhance the ability to design oligonucleotide drugs in the future.

Since genes are expressed at different times and in different cell types throughout an organism's life, it is important to know when, and how often, genes are expressed. Recombination knockout models only provides information about the first required expression event. In contrast, in the claimed model, because oligonucleotide administration can be performed at any time point during development, the identification of each burst of expression is enabled.

Varying the amount of oligonucleotide delivered to the embryo can provide useful information about the requirements of a cell (FIG. 3). Haplo-insufficiency, or the requirement of two copies of the gene to be active, is an important piece of information in genetic analysis. In addition, many human diseases are the result of an incomplete failure of gene expression. Recombination knockout provide an all or hall or nothing situation, which may not correspond to the expression level in the disease. By altering the dose of oligonucleotide in the present model, it is possible to duplicate any level of expression, from 0% to 100%.

Recent interest in the role of development genes in wound repair has led to the exploration of reactivated embryonic genes in the adult. Oligonucleotide-based knockout provides a unique model system to study activated expression of these regeneration-specific genes.

The blood-brain barrier represents the most difficult defense to breach both for pathogens and drugs. The barrier is not fully formed in the developing embryo, providing a powerful model for drug efficacy in the brain. Realistically, the embryo has no functioning immune system, but the control systems are activating the many complex pathways that result in a normal immune system. Disruption of many of these control systems will lead to the generation of models for a large number of immune system deficiencies and diseases.

The concept of knockouts is usually related to the inhibition or turning off of gene expression. However, in many instances, it is possible to upregulate expression. By inactivating a negative regulator, or repressor, a down-stream target of the repressor will be enhanced. Many diseases are a direct result of such interactions., and a knockout model of the invention can be constructed to study such genetic problems.

Various diseases can be studied (and therapeutics therefor tested) using this models including, but not limited to early onset Alzheimer's disease, B and T-cell maturation related disorders, and cancer. For example, the function of proto-oncogenes and tumor suppressor genes could be determined in this model. for function:

Many development genes are also involved in the development of cancer. The modulation of their expression in vivo represents a powerful tool to develop active therapeutic molecules for the treatment of cancer. Murine VEGF represents a clear example where functional data can be obtained in an in vivo system, and this data can be applied to the development of a new drug. The present model can also be used to optimize oligonucleotides as drugs in the treatment of cancer. A developmental model would provide ample flexibility in testing varied sequences and chemistries.

The model and methods of the invention also are useful for designing oligonucleotides as therapeutics agents in autoimmune diseases. Many adult autoimmune disorders can be linked to the presence of a specific allele of a gene. The presence of this allele constitutes susceptibility to the disease, and environmental factors can result in the manifestation of the disease. Diseases like Lupus, rheumatoid arthritis, ankylosing spondylitis, uveitis, and Crohn's disease are all linked to specific alleles of an essential immune system protein. Treating patients that express the allele could activate a feedback mechanism that would downregulate the dangerous molecule, reducing the risk of the disease.

The model can also be used to develop and evaluate antisense oligonucleotides useful to regulate expression of synthetic genes in developing embryos. There are many agricultural and veterinary applications to this type of effect. Treatment with oligonucleotides that target viral genes represents a means of establishing protection in an immature immune system.

The following examples illustrate the preferred modes of making and practicing the present invention, but are not meant to limit the scope of the invention since alternative methods may be utilized to obtain similar results.

EXAMPLE 1

Synthesis of the Oligodeoxynucleotide Phosphorothioates and Hybrid Oligonucleotides Phosphorothioate deoxynucleosides were synthesized on CPG on a 5–6 μmole scale on an automated synthesizer (model 8700, Millipore, Bedford, Mass.) using the H-phosphonate approach described in U.S. Pat. No. 5,149,798. Deoxynucleoside H-phosphonates were obtained from Millipore (Bedford, Mass.). 2'-O-methyl ribonucleotide H-phosphonates or phosphorothioates were synthesized by standard procedures (see, e.g., "Protocols for Oligonucleotides and Analogs" in *Meth. Mol. Biol.* (1993) Vol. 20) or commercially obtained (e.g., from Glenn Research, Sterling, Va. and Clontech, Palo Alto, Calif.). Segments of oligonucleotides containing 2'-O-methyl nucleoside(s) were assembled by using 2'-O-methyl ribonucleoside H-phosphonates or phosphorothioates for the desired cycles. Similarly, segments of oligonucleotides containing deoxyribonucleosides were assembled by using deoxynucleoside H-phosphonates for the desired cycles. After assembly, CPG bound oligonucleotide H-phosphonate was oxidized with sulfur to generate the phosphorothioate linkage. Oligonucleotides were then deprotected in concentrated $NH_4OH$ at 40° C. for 48 hours.

Crude oligonucleotide (about 500 $A_{260}$ units) is analyzed on reverse low pressure chromatography on a $C_{18}$ reversed phase medium. The DMT group is removed by treatment with 80% aqueous acetic acid, then the oligonucleotides were dialyzed against distilled water and lyophilized.

EXAMPLE 2

Transplacental Delivery of Oligonucleotides to Embryos

Pregnant outbred ICR mice at day 14 of gestation were obtained from Harlan Sprague Dawley (Indianapolis, Ind.). Animals were injected i.v. at a dose of 18 mg/kg with either a 21mer phosphorothioate (PS) DNA oligonucleotide (sequence 5' CAG CCT GGC TCA CCG CCT TGG (SEQ ID NO:1), a 21mer 4×4 hybrid PS oligonucleotide (sequence 5' <u>CAG C</u>CT GGC TCA CCG CC<u>U UGG</u>, (SEQ ID NO:2) (underlined, sequence being 2'-O-methyl RNA) targeted to mVEGF); or a mismatch chemistry control oligonucleotide. Animals were sacrificed 24 or 48 hours later and kidney, liver, spleen and embryos collected. The tissues were weighed and homogenized in 5 mM NaCl; 10 mM Tris, pH 8.0; 6.4 mM EDTA; 2 mM NaOH; 16 mM SDS to give a 10% suspension. To 50 μl homogenate was added 10 μl of a 20 mg/ml solution of proteinase K (Sigma Chemical Company, St. Louis) and incubated at 60° C. for 2 hours, then 95° C. for 15 minutes. 10 μl of digest was mixed with 160 μl of 10% v/v/serum; 0.5% v/v NP40; 0.9% w/v NaCl. This was analyzed by anion exchange HPLC using a Hewlett Packard Company model HP-1090 instrument. Material was eluted in a salt gradient of 0.5–2.0 M LiBr in 25 mM Tris-HCl, pH 10.5; 2 mM EDTA and detected by UV absorbance at 270 nm. The concentration of oligonucleotide in the tissues was extrapolated from a calibration curve derived from known concentrations of the original oligonucleotide. The results are shown in FIG. 1.

Confirmation studies were performed on mice at day 6 or day 7 of gestation using the same hybrid PS oligonucleotide (SEQ ID NO:2) and a hybrid chemistry control oligonucleotide (which is a mismatch oligonucleotide directed to a different region of the VEGF gene) at the same dose. The embryos were removed five days later or at birth for analysis.

EXAMPLE 3

Transplacental Delivery of Oligonucleotides Targeting the Mouse E-cadherin Gene

The mouse epithelial cadherin (E-cadherin) gene was targeted with an antisense oligonucleotide previously described in the literature (Chen, B. and Hales, B. F. (1995) *Biology of Reproduction*, 53: 1229–1238). Pregnant outbred ICR mice at day 10 of gestation were obtained from Harlan Sprague Dawley (Indianapolis, Ind.). Animals were injected i.v. at a dose of 18 mg/kg with either a 21mer 4×4 hybrid PS oligonucleotide (sequence 5' <u>GGA AAA</u> GCT GCG GC<u>A CCG</u> 3', (SEQ ID NO:3) (underlined sequence being 2'-O-methyl RNA) targeted to mouse E-cadherin); or a mismatch chemistry control oligonucleotide (E-cad-mm; SEQ ID NO. 10). Animals were sacrificed on day 12 of gestation and the embryos were removed and examined (FIG. 2).

The observed phenotypes were identical to those previously reported in a rat whole embryo culture system and are summarized as follows: All the control embryos were normal (n=12). In the embryos treated with E-cadherin antisense oligonucleotide, all were developmentally arrested (n=19), 17 had enlarged hindbrain, one had no hindbrain, 14 had rhomboencephalon edema, 15 had enlarged pericardium, and 7 had neural tube closure defects.

EXAMPLE 4

Transplacental Delivery of Oligonucleotides to Embryos Targeting the Mouse VEGF Gene Timed pregnant Swiss-Webster mice were injected with a single dose of oligonucleotide at different times during development. 29 oligonucleotide sequences and chemical modifications were tested. Phosphorothioate oligonucleotides did not produce any observable effects in either the adult or in the embryos. A single injection of the 2'-O-methyl phosphorothioate modified oligonucleotides, Vm, M3, M13 and H3 (Robinson, personal observation) (FIG. 3) at 18 mg/kg body weight at E7.5–E8.5 each duplicated the loss of function phenotype of VEGF with no observable toxic effects on the adult.

Injections of oligonucleotide from E6–7.0 had no effect. For the remainder of primary angiogenesis, E9 to E12, the oligonucleotide treatment had no effect; the embryos developed normally.

The loss of angiogenesis phenotype (E7.5–8.5) was indistinguishable from published reports of the recombinant knockout (Ferrara and Davis-Smith (1997) *Endocrine Reviews* 18:4–25; Carmeliet et al. (1996) *Nature* 380:435–439). Yolk sac vasculature was not apparent in the active oligonucleotide-treated animals, the size of the embryos averaged 60% of wild type and craniofacial malformations were consistent with the knockout. Analysis of the morphology of E10–12.5 embryos showed suspended development at E10.5, resulting in retarded tissue development and loosely organized blood vessels. The only noted difference from the knockout phenotype was a lack of increased apoptosis associated with the E10.5 lethality observed in histological sections.

Vm (SEQ ID NO. 4), M3 (SEQ ID NO. 5) and M13 (SEQ ID NO. 6) are murine-specific antisense oligonucleotides, while H3 (SEQ ID. NO. 7) is based on human VEGF sequence, and contains a single base mismatch to the murine sequence. All four of the active oligonucleotides generated the same phenotype and diluted with the same kinetics. Neither a sense control for Vm nor a five-base mismatch to Vm (Vm-mm; SEQ ID NO. 8), M3 (M3-mm; SEQ ID NO. 11), M13 (M13-mm; SEQ ID NO. 12) or H3 (H3-mm; SEQ ID NO. 9) produced any observable effect. None of twenty-four additional oligonucleotides examined, including four 2'-O-methyl oligonucleotides, sixteen phosphorothioate oligonucleotides, two methyl phosphonate modified oligonucleotides and two inverted chimeric oligonucleotides (data not shown), generated any observable phenotypic changes from wild type. This suggests that both sequence and chemistry are essential factors of activity.

Single injections of Vm or H3 from E12–E19 uncovered a secondary VEGF phenotype, resulting in dehydration and an enlarged bladder. The timing of injection was critical; prior to E16, no effect was observed, but from E16.5 through E19, a dose of the active inhibitor resulted in perinatal lethality (P2.5) with a grossly enlarged bladder. Control oligonucleotides did not induce any kidney defects and were indistinguishable from wild type. Hematoxylin and eosin stained kidney sections revealed no change in histological architecture of the glomeruli, nephrons or associated vessels. This phenotype is in marked contrast to VEGF antibody treatment, which resulted in disrupted vessel formation and a decrease in numbers of nephrons and glomeruli (Kitamoto, 1997). Interestingly, inhibition of VEGF between E16.5 and birth did not affect the proliferation of endothelial cells and the formation of blood vessels within the kidney. The kidney defect induced by oligonucleotide based inhibition is suggestive of VEGF's role as the vascular permeability factor.

EXAMPLE 5

Transplacental Delivery of Oligonucleotide Targeting the Mouse E-cadherin Gene

To determine transplacental delivery, oligonucleotide levels in the embryos were measured by HPLC (FIG. 1), and found to be comparable to levels in the spleen of the adult, indicating that the placenta is not a barrier to the compounds. Both placental uptake and generation of a knockout phenotype were dependent on oligonucleotide sequence and chemistry, and were gene specific. To assay for specific antisense mRNA inhibitory activity of the oligonucleotide, adult animals with E7.5 or E8.5 embryos were injected IP with a single dose at 20 mg oligonucleotide/kg body weight. The embryos were harvested 6 hours post injection. Total RNA was extracted from the embryos, treated with DNase and assayed for VEGF mRNA using real-time quantitative PCR (PE-ABI Prism 7700 SDS). The levels of VEGF mRNA from untreated, control treated and Vm-treated litters were measured relative to a reference standard, cyclophilin. In Vm-treated E7.5+6 hr embryos, there was a 54% decrease in VEGF mRNA relative to non-specific oligonucleotide-treated controls (data not shown). This data supports the model that oligonucleotide based inhibition of VEGF is specifically reducing the level of the VEGF mRNA.

EXAMPLE 6

Transplacental Deliver of Antisense Oligonucleotide Targeting the Mouse E-cadherin Gene To assess the gene-specificity of oligonucleotide based inhibition for a second gene, E-cadherin was tested. The loss of function of E-cadherin has been characterized (Takeichi et al. (1988) *Development* 102:639–655, Anderson et al.

(1990) *Experimentia* 46:2–13). The E-cadherin knockout suffers a compaction deficiency. Maternal E-cadherin is sufficient to induce compaction, but the E-cadherin (-/-) background cannot maintain the compacted state and does not form a blastocoel. Synthetic antisense oligonucleotides were generated and introduced by amniotic microinjection into E10 embryos in culture, resulting in a neural tube defect in E12 embryos (Chen, B. and Hales, B. F. (1995) *Biology of Reproduction*, 53: 1229–1238). This same neural tube defect was observed using oligonucleotide based inhibition to E-cadherin in utero.

An active E-cadherin oligonucleotide was synthesized containing a phosphorothioate backbone with partial 2'-O-methyl modified bases, similar in construction to the active VEGF oligonucleotides (FIG. 2). As a control, a four-base mismatch was generated that preserved the purine/pyrimidine ratio of the oligonucleotide (E-cad-mm; SEQ ID NO. 10). Pregnant adults were treated at E10 and the embryos were harvested at E12.5. Each of the phenotypes described previously was identified. The principle effects were rhombencephalon edema (swollen hindbrain), neural tube closure defects and developmental arrest. The control oligonucleotide had no effect in the embryos. Importantly, the developmental defects defined by oligonucleotide based inhibition of E-cadherin are separate and distinct from those defined by oligonucleotide based inhibition of VEGF. The vasculature of the yolk sac and the embryos was normal, the cranio-facial malformations were characteristic of the E-cadherin phenotype, and the overall developmental arrest was markedly different., roughly 80% of wild type.

Summary of Sequence Listings

```
SEQ.ID NO.1   Vm         CAG CCT GGC TCA CCG CCT TGG
SEQ.ID NO.2   Vm         CAG CCT GGC TCA CCG CCU UGG
SEQ.ID NO.3   E-cad      GGA AAA GCT GCG GCA CCG
SEQ.ID NO.4   Vm         CAG CCT GGC TCA CCG CCT TGG
SEQ.ID NO.5   M3         TCG CGC TCC CTC TCT CCG GC
SEQ.ID NO.6   M13        CGC TCC CTC TCT CCG GCT CG
SEQ.ID NO.7   H3         CAC CCA AGA CAG CAG AAA G
SEQ.ID NO.8   Vm-mm      CAA CTT AGC TTA CCG CCT TAG
SEQ.ID NO.9   H3-mm      CAT CCG AGG CAA CAA AAA G
SEQ.ID NO.10  E-cad-mm   GGA CAA GAT CCG GCA GCG
SEQ.ID NO.11  M3-mm      TCA CGT TCC TTC TCC CCA GC
SEQ.ID NO.12  M13-mm     CGT TCT CTC CCT CCA GCC CG
```

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of determining the function of a gene expressed in a mouse, comprising:

(a) transplacentally delivering to a mouse embryo a synthetic oligonucleotide effective in modulating the expression of the gene by systemically administering to a pregnant mouse in which the embryo is present the oligonucleotide in a pharmaceutically acceptable carrier, wherein the synthetic oligonucleotide comprises:

(i) RNA or a combination of RNA and DNA;

(ii) a stabilized backbone, comprising phophorothioate internucleotide linkages; and (iii) at least one 2'-O-alkyl ribonucleotide, the alkyl being a saturated alkyl; and (b) determining whether the phenotype of the embryo is altered, the altered phenotype of the embryo being indicative of the function of the gene.

2. A method of delivering a synthetic oligonucleotide to a mouse embryo, comprising systemically administering to a pregnant mouse in which the embryo is present the oligonucleotide and a pharmaceutically acceptable carrier, wherein the synthetic oligonucleotide comprises:

(a) RNA or a combination of RNA and DNA;

(b) a stabilized backbone, comprising phophorothioate internucleotide linkages; and (c) at least one 2'-O-alkyl ribonucleotide, the alkyl being a saturated alkyl; wherein the oligonucleotide passes through the placenta into the embryo.

3. The method of claim 1 or 2, wherein the 2'-O-alkyl ribonucleotide is a 2'-O-methyl ribonucleotide.

4. The method of claim 1 or 2, wherein the oligonucleotide comprises at least one 2'-O-alkyl ribonucleotide at its 3' terminus and at least one 2'-O-alkyl ribonucleotide at its 5' terminus.

5. The method of claim 1 or 2, wherein the oligonucleotide comprises at least two 2'-O-alkyl ribonucleotides at its 3' terminus and at least two 2'-O-alkyl ribonucleotides at its 5' terminus.

6. The method of claim 1 or 2, wherein the oligonucleotide comprises at least four 2'-O-alkyl ribonucleotides at its 3' terminus and at least four 2'-O-alkyl ribonucleotides at its 5' terminus.

7. The method of claim 1 or 2, wherein the gene is the VEGF gene.

8. The method of claim 1 or 2, wherein the gene is the E-cadherin gene.

9. The method of claim 1 or 2, wherein the oligonucleotide passes through the placenta into the embryo in intact form.

10. The method of claim 1 or 2, wherein transplacental delivery of the oligonucleotide is performed at any time during gestation.

* * * * *

SEQUENCE LISTING

```
<160> NUMBER OF SEQ ID NOS:  12

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:Vm
      oligonucleotide
<223> OTHER INFORMATION: Description of Artificial Sequence:synthetic
      oligonucleotide

<400> SEQUENCE: 1
cagcctggct caccgccttg g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:Vm
      oligonucleotide
<223> OTHER INFORMATION: Description of Artificial Sequence:synthetic
      oligonucleotide

<400> SEQUENCE: 2
cagcctggct caccgccuug g                                              21

<210> SEQ ID NO 3
<211> LENGTH: 18
```

```
<212> TYPE: DNA
<213> ORGANISM: Artificial Sequence
<220> FEATURE:
<223> OTHER INFORMATION: Description of Combined DNA/RNA Molecule:E-cad
      oligonucleotide
<223> OTHER INFORMATION: Description of Artificial Sequence:synthetic
      oligonucleotide

<400> SEQUENCE: 3
ggaaaagctg cggcaccg                                              18

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:Vm
      oligonucleotide
<223> OTHER INFORMATION: Description of Artificial Sequence:synthetic
      oligonucleotide

<400> SEQUENCE: 4
cagcctggct caccgccttg g                                          21

<210> SEQ ID NO 5
<211> LENGTH: 20
<212> TYPE: DNA
<213> ORGANISM: Artificial Sequence
<220> FEATURE:
<223> OTHER INFORMATION: Description of Combined DNA/RNA Molecule:M3
      oligonucleotide
<223> OTHER INFORMATION: Description of Artificial Sequence:synthetic
      oligonucleotide

<400> SEQUENCE: 5
tcgcgctccc tctctccggc                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Combined DNA/RNA Molecule:M13
      oligonucleotide
<223> OTHER INFORMATION: Description of Artificial Sequence:synthetic
      oligonucleotide

<400> SEQUENCE: 6
cgctccctct ctccggctcg                                            20

<210> SEQ ID NO 7
<211> LENGTH: 19
<212> TYPE: DNA
<213> ORGANISM: Artificial Sequence
<220> FEATURE:
<223> OTHER INFORMATION: Description of Combined DNA/RNA Molecule:H3
      oligonucleotide
<223> OTHER INFORMATION: Description of Artificial Sequence:synthetic
      oligonucleotide

<400> SEQUENCE: 7
cacccaagac agcagaaag                                             19

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:Vm-mm
```

```
        oligonucleotide
<223> OTHER INFORMATION: Description of Artificial Sequence:synthetic
      oligonucleotide

<400> SEQUENCE: 8
caacttagct taccgcctta g                                              21

<210> SEQ ID NO 9
<211> LENGTH: 19
<212> TYPE: DNA
<213> ORGANISM: Artificial Sequence
<220> FEATURE:
<223> OTHER INFORMATION: Description of Combined DNA/RNA Molecule:H3-mm
      oligonucleotide
<223> OTHER INFORMATION: Description of Artificial Sequence:synthetic
      oligonucleotide

<400> SEQUENCE: 9
catccgaggc aacaaaaag                                                 19

<210> SEQ ID NO 10
<211> LENGTH: 18
<212> TYPE: DNA
<213> ORGANISM: Artificial Sequence
<220> FEATURE:
<223> OTHER INFORMATION: Description of Combined DNA/RNA Molecule:
      E-cad-mm oligonucleotide
<223> OTHER INFORMATION: Description of Artificial Sequence:synthetic
      oligonucleotide

<400> SEQUENCE: 10
ggacaagatc cggcagcg                                                  18

<210> SEQ ID NO 11
<211> LENGTH: 20
<212> TYPE: DNA
<213> ORGANISM: Artificial Sequence
<220> FEATURE:
<223> OTHER INFORMATION: Description of Combined DNA/RNA Molecule:M3-mm
      oligonucleotide
<223> OTHER INFORMATION: Description of Artificial Sequence:synthetic
      oligonucleotide

<400> SEQUENCE: 11
tcacgttcct tctccccagc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Combined DNA/RNA Molecule:M13-mm
      oligonucleotide
<223> OTHER INFORMATION: Description of Artificial Sequence:synthetic
      oligonucleotide

<400> SEQUENCE: 12
cgttctctcc ctccagcccg                                                20
```